United States Patent
Cohen

(10) Patent No.: US 11,903,940 B2
(45) Date of Patent: *Feb. 20, 2024

(54) METHODS OF TREATING DISEASE WITH LEVOKETOCONAZOLE

(71) Applicant: Strongbridge Dublin Limited, Trevose, PA (US)

(72) Inventor: Fredric Cohen, Washington Crossing, PA (US)

(73) Assignee: Strongbridge Dublin Limited, Trevose, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/655,632

(22) Filed: Mar. 21, 2022

(65) Prior Publication Data

US 2022/0387425 A1    Dec. 8, 2022

Related U.S. Application Data

(63) Continuation of application No. 17/319,781, filed on May 13, 2021, now Pat. No. 11,278,547, which is a continuation of application No. 17/010,387, filed on Sep. 2, 2020, now Pat. No. 11,020,393, which is a continuation of application No. PCT/US2020/020644, filed on Mar. 2, 2020.

(60) Provisional application No. 62/813,399, filed on Mar. 4, 2019.

(51) Int. Cl.
*A61K 31/497* (2006.01)
*A61K 31/155* (2006.01)

(52) U.S. Cl.
CPC .......... *A61K 31/497* (2013.01); *A61K 31/155* (2013.01)

(58) Field of Classification Search
None
See application file for complete search history.

(56) References Cited

U.S. PATENT DOCUMENTS

| | | |
|---|---|---|
| 9,918,984 B2 | 3/2018 | Marin |
| 10,005,759 B2 | 6/2018 | Bersot et al. |
| 10,098,877 B2 | 10/2018 | Marin |
| 10,214,507 B2 | 2/2019 | Bersot et al. |
| 10,512,667 B2 | 12/2019 | Kerppola et al. |
| 10,517,868 B2 | 12/2019 | Marin |
| 10,835,530 B2 | 11/2020 | Marin |
| 11,020,393 B2 | 6/2021 | Cohen |
| 11,278,547 B2 | 3/2022 | Cohen |
| 2018/0153883 A1 | 6/2018 | Marin |
| 2018/0338971 A1 | 11/2018 | Koziol |
| 2020/0397781 A1 | 12/2020 | Cohen |

FOREIGN PATENT DOCUMENTS

| | | |
|---|---|---|
| WO | WO-2016048984 A1 | 3/2016 |
| WO | WO-2018106907 A1 | 6/2018 |

OTHER PUBLICATIONS

Kimura et al., "Metformin is a Superior Substrate for Renal Organic Cation Transporter OCT2 rather than Hepatic OCT1", 2005, Drug Metab. Pharmacokinet., 20(5), pp. 379-386. (doi: 10.2133/dmpk.20.379) (Year: 2005).*
Caffrey et al., "The art and science of drug titration", 2020, Therapeutic Advances in Drug Safety, vol. 11, pp. 1-14. (Year: 2020).*
Carmichael, J. et al., "Making the diagnosis of cyclic Cushing's syndrome: a position statement from the topic editors", Neurosurg Focus, 38(2):E8, American Association of Neurological Surgeons, United States (2015).
Fleseriu, M. et al., "Results From the Phase 3 Multicenter Sonics Study of Levoketoconazole: Subgroup Analysis of Cushing's Syndrome Patients With Diabetes Mellitus", Endocrine Society Annual Meeting, poster SAT-452; 1 page, (2019).
Flory, J. et al., "Metformin in 2019", JAMA 321(19): 1926-7, American Medical Association, United States (2019).
International Preliminary Report on Patentability for International Application No. PCT/US2020/020644, The International Bureau of WIPO, dated Sep. 16, 2021, 8 pages.
International Search Report and Written Opinion for International Application No. PCT/US2020/020644, ISA/US, dated Jun. 23, 2020, 11 pages.
Mayo Clinic, "Metformin (Oral Route) Description and Brand Names", Accessed Feb. 4, 2021, https://www.mayoclinic.org/drugs-supplements/metformin-oral-route/description/drg-20067074. (2021).
Rossi, K., "Phase 3 Trial of Endogenous Cushing's Syndrome Treatment Meets Primary Endpoints", HCP Live; https://www.mdmag.com/medical-news/phase-3-trial-endogenous-cushingsyndrome-treatment-meets-primary-endpoints-, 2 pages, (2018).
Schuck, R. et al., "Use of Titration as a Therapeutic Individualization Strategy: An Analysis of Food and Drug Administration—Approved Drugs", Clin Transl Sci. 12(3):236-9, Wiley-Blackwell, United States (2019).
Schwartz, S. et al., "Safety profile and metabolic effects of 14 days of treatment with DIO-902: results of a phase IIa multicenter, randomized, double-blind, placebo-controlled, parallel-group trial in patients with type 2 diabetes mellitus", Clin Ther. 30(6):1081-8, Elsevier, Netherlands (2008).
Tritos, N. et al., "Medical Management of Cushing Disease", Neurosurg Clin N Am., 30(4):499-508, Elsevier, Netherlands (2019).
Shih, W.J., et al., "The analysis of titration studies in phase III clinical trials," Stat Med 8(5):583-91, Wiley, United States (May 1989).
Sundaram, N., et al., "Characterization of persistent and recurrent Cushing's disease," Pituitary 17(4):381-91, Springer, Germany (Aug. 2014).

(Continued)

*Primary Examiner* — Kevin E Weddington
(74) *Attorney, Agent, or Firm* — Sterne, Kessler, Goldstein & Fox P.L.L.C.

(57) ABSTRACT

Provided herein is a method of administering levoketoconazole, or a pharmaceutically acceptable salt thereof, to a subject in need thereof, wherein the subject is also being administered a multidrug and toxin extrusion transporter 1 (MATE1) substrate or an organic cation transporter 2 (OCT2) substrate.

18 Claims, No Drawings

(56) References Cited

OTHER PUBLICATIONS

The National Institute of Diabetes and Digestive and Kidney Diseases (NIDDK), "Cushing's Syndrome", accessed at www.niddk.nih.gov/health-information/endocrine-disease/cushings-syndrome, 11 pages (2018).

Pivonello, R., et al., "Levoketoconazole in the Treatment of Patients With Cushing's Syndrome and Diabetes Mellitus: Results From the SONICS Phase 3 Study," Front Endocrinol 12:595894, Frontiers Media, Switzerland (Apr. 2021).

Fleseriu, M., et al., "Levoketoconazole: a novel treatment for endogenous Cushing's syndrome," *Expert Review of Endocrinology & Metabolism* 16(4):159-174, Taylor & Francis, United Kingdom (Jun. 2021).

\* cited by examiner

METHODS OF TREATING DISEASE WITH LEVOKETOCONAZOLE

This application is a continuation of U.S. patent application Ser. No. 17/010,387, filed Sep. 2, 2020, which is a continuation of International Application No. PCT/US2020/020644, filed Mar. 2, 2020, which claims the benefit of priority of U.S. Provisional Patent Application Ser. No. 62/813,399 filed Mar. 4, 2019, the disclosures of which are incorporated by reference in their entireties for all purposes.

Endogenous Cushing's disease is a rare, serious, and potentially lethal endocrine disease caused by excessive exposure of organs to cortisol. In about 80% of patients, excessive secretion of adrenocorticotrophic hormone (ACTH) causes Cushing's syndrome, most commonly via a pituitary corticotropic adenoma and less often via an extrapituitary tumor (ectopic ACTH syndrome) or, in rare instances, by an ectopic corticotropin-releasing hormone-secreting tumor. In the remaining 20% of patients, Cushing's syndrome is ACTH-independent and is caused by excess cortisol secretion by unilateral adrenocortical tumors, bilateral adrenal hyperplasia, or dysplasia.

Nizoral™ (ketoconazole) is approved in the US as an antifungal agent for certain systemic and recalcitrant skin fungal infections. Ketoconazole HRA® contains ketoconazole and is registered in some countries outside the US as a treatment for Cushing's syndrome. Ketoconazole reduces or inhibits adrenal steroid production by inhibiting several adrenal steroidogenic enzymes, including CYP17A1 (also known as 17α-hydroxylase) and CYP11B1 (also known as mitochondrial 11β-hydroxylase). A direct effect on ectopic ACTH has also been observed in vitro. The efficacy of ketoconazole in treating Cushing's syndrome has not been the subject of a large prospective clinical trial, although it has been the subject of several small open-label trials and larger retrospective case series. Ketoconazole reportedly normalizes hypercortisolism in 30-70% of patients and reduces complications of excessive cortisol, including diabetes and hypertension, and other signs and symptoms of Cushing's syndrome.

Ketoconazole, however, has several known risks, including hepatotoxicity. Elevated levels of transaminases are common. Ketoconazole also potently inhibits several drug-metabolizing enzymes, including CYP3A4, with a potential for marked drug interactions, including those leading to increased risk for QT prolongation. Despite the availability of two FDA-approved drugs, ketoconazole continues to be commonly used off-label for treating Cushing's syndrome in the US, and by some accounts is the most frequently prescribed medical therapy for Cushing's syndrome, reflecting the persistent need unmet by approved therapies.

Levoketoconazole (Recorlev™, COR-003, 2S,4R cis-1-acetyl-4-[4-[[2-(2,4-dichlorophenyl)-2-(1H-imidazol-1-yl-methyl)-1,3-dioxolan-4-yl]methoxyl]phenyl]piperazine) is an investigational cortisol synthesis inhibitor. Levoketoconazole is the 2S,4R enantiomer of ketoconazole. Non-clinical and clinical data suggest that compared with the 2R,4S enantiomer of ketoconazole, levoketoconazole more potently inhibits cortisol synthesis, and reaches higher plasma concentrations after ketoconazole dosing.

Provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the subject is also being co-administered a therapeutically effective amount of a multidrug and toxin extrusion transporter 1 (MATE1) substrate or an organic cation transporter 2 (OCT2) substrate;

wherein the therapeutically effective amount of levoketoconazole, or a pharmaceutically acceptable salt thereof, is determined via a titration scheme, and wherein the therapeutically effective amount of the MATE1 substrate or OCT2 substrate, is reduced relative to a subject who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers in a subject in need thereof, wherein the subject is being co-administered a therapeutically effective amount of a multidrug and toxin extrusion transporter 1 (MATE1) substrate or an organic cation transporter 2 (OCT2) substrate, comprising:

reducing the amount of MATE1 substrate or OCT2 substrate being administered to the subject, and subsequently initiating administration of a therapeutically effective amount of levoketoconazole, or a pharmaceutically acceptable salt thereof wherein the therapeutically effective amount of levoketoconazole, or a pharmaceutically acceptable salt thereof, is determined via a titration scheme.

In some embodiments, reducing the amount of MATE1 substrate or OCT2 substrate being administered to the subject comprises discontinuing administration of the MATE1 substrate or OCT2 substrate.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the subject is also being co-administered a therapeutically effective amount of metformin, or a pharmaceutically acceptable salt thereof;

wherein the therapeutically effective amount of levoketoconazole, or a pharmaceutically acceptable salt thereof, is determined via a titration scheme, and wherein the therapeutically effective amount of metformin, or a pharmaceutically acceptable salt thereof, is reduced relative to a subject who is not being administered levoketoconazole, or a pharmaceutically acceptable salt thereof.

In some embodiments, reducing the amount of metformin being administered to the subject comprises discontinuing administration of the metformin.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers in a subject in need thereof, wherein the subject is being co-administered a therapeutically effective amount of metformin, comprising:

reducing the amount of metformin being administered to the subject, and subsequently initiating administration of a therapeutically effective amount of levoketoconazole, or a pharmaceutically acceptable salt thereof wherein the therapeutically effective amount of levoketoconazole, or a pharmaceutically acceptable salt thereof, is determined via a titration scheme.

Also provided is a method of treating a disease chosen from Cushing's disease, syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and subsequently determining that the patient is to begin treatment with a multidrug and toxin extrusion transporter 1 (MATE1) substrate or an organic cation transporter 2 (OCT2) substrate, wherein MATE1 substrate or OCT2 substrate, is administered in an amount that is less than the amount that would be administered to a patient who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and subsequently determining that the patient is to begin treatment with metformin, wherein the metformin is administered in an amount that is less than the amount that would be administered to a patient who is not being administered levoketoconazole, or a pharmaceutically acceptable salt thereof.

In some embodiments, the starting dose is less than the amount that would be administered to a patient who is not being administered levoketoconazole, or a pharmaceutically acceptable salt thereof. In some embodiments, the starting dose is increased by an incremental amount (e.g., 250 mg) that is less than the amount that would be used with a patient who is not being administered levoketoconazole, or a pharmaceutically acceptable salt thereof (e.g., 500 mg).

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, in a subject in need thereof, wherein the subject is also being administered metformin, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and wherein the administration of levoketoconazole, or a pharmaceutically acceptable salt thereof, increases the systemic exposure to metformin by about 2-fold.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

When introducing elements of the present disclosure or the embodiment(s) thereof, the articles "a", "an", "the" and "said" are intended to mean that there are one or more of the elements. The terms "comprising", "including" and "having" are inclusive and mean that there may be additional elements other than the listed elements.

The term "and/or" when in a list of two or more items, means that any of the listed items can be employed by itself or in combination with one or more of the listed items. For example, the expression "A and/or B" means either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about" qualifies the numerical values that it modifies, denoting such a value as variable within a margin of error. When no margin of error, such as a standard deviation to a mean value given in a chart or table of data, is recited, the term "about" means that range which would encompass the recited value and the range which would be included by rounding up or down to that figure, considering significant figures.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treating a disease or disorder or on the effecting of a clinical endpoint.

The term "therapeutically acceptable" refers to those compounds suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease. In certain embodiments, prevention of a disease may involve prevention of attacks of an intermittent nature, as well as prevention of a permanent state of muscle weakness, such as an irreversible state of impairment owing to underlying disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

As used herein, a patient is said to "tolerate" a dose of a compound if administering that dose to that patient does not result in an unacceptable adverse event or an unacceptable combination of adverse events. One of skill in the art will appreciate that tolerance is a subjective measure and that what may be tolerable to one patient may not be tolerable to a different patient. For example, one patient may not be able to tolerate headache, whereas a second patient may find headache tolerable but is not able to tolerate vomiting, whereas for a third patient, either headache alone or vomiting alone is tolerable, but the patient is not able to tolerate the combination of headache and vomiting, even if the severity of each is less than when experienced alone.

As used herein, an "adverse event" is an untoward medical occurrence associated with treatment with a pharmaceutical agent.

As used herein, the term "hormone-sensitive cancer" refers to any cancer which may be affected by a hormone; hormones typically increase proliferation of hormone-sensitive cancers.

As used herein, "up-titration" of a compound refers to increasing the amount of a compound to achieve a therapeutic effect that occurs before dose-limiting intolerability for the patient. Up-titration can be achieved in one or more dose increments, which may be the same or different.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Metformin refers to N,N-dimethylimidodicarbonimidic diamide hydrochloride. A formulation of metformin has been previously reported in the FDA approved drug label GLUCOPHAGE as an adjunct to diet and exercise to improve glycemic control in adults with type 2 diabetes mellitus.

GLUCOPHAGE tablets contain 500 mg, 850 mg, or 1000 mg of metformin hydrochloride, which is equivalent to 389.93 mg, 662.88 mg, 779.86 mg metformin base, respectively. Each tablet contains the inactive ingredients povidone and magnesium stearate. In addition, the coating for the 500 mg and 850 mg tablets contains hypromellose and the coating for the 1000 mg tablet contains hypromellose and polyethylene glycol. GLUCOPHAGE XR contains 500 mg or 750 mg of metformin hydrochloride, which is equivalent to 389.93 mg, 584.90 mg metformin base, respectively. GLUCOPHAGE XR 500 mg tablets contain the inactive ingredients hypromellose, microcrystalline cellulose, sodium carboxymethyl cellulose, and magnesium stearate. GLUCOPHAGE XR 750 mg tablets contain the inactive ingredients hypromellose, sodium carboxymethyl cellulose, magnesium stearate and iron oxide pigment red.

The standard dosages for metformin are:
Adult Dosage for GLUCOPHAGE:
Starting dose: 500 mg orally twice a day or 850 mg once a day, with meals
Increase the dose in increments of 500 mg weekly or 850 mg every 2 weeks, up to a maximum dose of 2550 mg per day, given in divided doses
Doses above 2000 mg may be better tolerated given 3 times a day with meals
Adult Dosage for GLUCOPHAGE XR:
Starting dose: 500 mg orally once daily with the evening meal
Increase the dose in increments of 500 mg weekly, up to a maximum of 2000 mg once daily with the evening meal
Patients receiving GLUCOPHAGE may be switched to GLUCOPHAGE XR once daily at the same total daily dose, up to 2000 mg once daily
Pediatric Dosage for GLUCOPHAGE:
Starting dose: 500 mg orally twice a day, with meals
Increase dosage in increments of 500 mg weekly up to a maximum of 2000 mg per day, given in divided doses twice daily An oral solution of metformin has also been approved. It contains 500 mg of metformin hydrochloride per 5 mL and the following inactive ingredients: Saccharin Calcium, Potassium Bicarbonate, Xylitol, Hydrochloric Acid, Purified Water and Cherry Flavor The maximum recommended daily dose is 2550 mg (25.5 mL) in adults and 2000 mg (20 mL) in pediatric patients (10-16 years of age).

Provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the subject is also being co-administered a therapeutically effective amount of a multidrug and toxin extrusion transporter 1 (MATE1) substrate or an organic cation transporter 2 (OCT2) substrate;

wherein the therapeutically effective amount of levoketoconazole, or a pharmaceutically acceptable salt thereof, is determined via a titration scheme, and wherein the therapeutically effective amount of the MATE1 substrate or OCT2 substrate, is reduced relative to a subject who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers in a subject in need thereof, wherein the subject is being co-administered a therapeutically effective amount of a multidrug and toxin extrusion transporter 1 (MATE1) substrate or an organic cation transporter 2 (OCT2) substrate, comprising:

reducing the amount of MATE1 substrate or OCT2 substrate being administered to the subject, and subsequently initiating administration of a therapeutically effective amount of levoketoconazole, or a pharmaceutically acceptable salt thereof wherein the therapeutically effective amount of levoketoconazole, or a pharmaceutically acceptable salt thereof, is determined via a titration scheme.

In some embodiments, reducing the amount of MATE1 substrate or OCT2 substrate being administered to the subject comprises discontinuing administration of the MATE1 substrate or OCT2 substrate.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the subject is also being co-administered a therapeutically effective amount of metformin, or a pharmaceutically acceptable salt thereof;

wherein the therapeutically effective amount of levoketoconazole, or a pharmaceutically acceptable salt thereof, is determined via a titration scheme, and wherein the therapeutically effective amount of metformin, or a pharmaceutically acceptable salt thereof, is reduced relative to a subject who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers in a subject in need thereof, wherein the subject is being co-administered a therapeutically effective amount of metformin, comprising:

reducing the amount of metformin being administered to the subject, and subsequently initiating administration of a therapeutically effective amount of levoketoconazole, or a pharmaceutically acceptable salt thereof wherein the therapeutically effective amount of levoketoconazole, or a pharmaceutically acceptable salt thereof, is determined via a titration scheme.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and subsequently determining that the patient is to begin treatment with a multidrug and toxin extrusion transporter 1 (MATE1) substrate or an organic cation transporter 2 (OCT2) substrate, wherein MATE1 substrate or OCT2 substrate, is administered in an amount that is less than the amount that would be administered to a patient who is not being administered levoketoconazole, or a pharmaceutically acceptable salt thereof.

Also provided is a method of treating a disease chosen from Cushing's disease, syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and subsequently determining that the patient is to begin treatment with a multidrug and toxin extrusion transporter 1 (MATE1) substrate or an organic cation transporter 2 (OCT2) substrate, wherein MATE1 substrate or OCT2 substrate is administered at a starting dose that is less than the amount that would be administered to a patient who is not being administered levoketoconazole, or a pharmaceutically acceptable salt thereof.

In some embodiments, the method further comprises increasing the starting dose by an amount that is less than the amount that would be administered to a patient who is not being administered levoketoconazole, or a pharmaceutically acceptable salt thereof. In some embodiments, the method further comprises increasing the starting dose by 250 mg increments as compared with the 500 mg increments that would be administered to a patient who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and subsequently determining that the patient is to begin treatment with metformin, wherein the metformin is administered in an amount that is less than the amount that would be administered to a patient who is not being administered levoketoconazole, or a pharmaceutically acceptable salt thereof.

Also provided is a method of treating a disease chosen from Cushing's disease, Cushing's syndrome, cyclic Cushing's syndrome, exogenous hypercortisolism, hypercortisolism, hyperglycemia, multiple endocrine neoplasia type 1, McCune Albright syndrome, Carney complex, congenital adrenal hyperplasia, precocious puberty, and hormone-sensitive cancers, in a subject in need thereof, wherein the subject is also being administered metformin, comprising:

administering a therapeutically effective amount of levoketoconazole, or a pharmaceutically acceptable salt thereof, to a subject in need thereof, wherein the therapeutically effective amount of levoketoconazole, or a pharmaceutically acceptable salt thereof, is determined via a titration scheme, and wherein the administration of levoketoconazole, or a pharmaceutically acceptable salt thereof, increases the systemic exposure to metformin by about 2-fold.

In certain embodiments, the disease is Cushing's syndrome. In certain embodiments, the disease is cyclic Cushing's syndrome. In certain embodiments, the disease is persistent or recurrent Cushing's syndrome. In certain embodiments, the subject has had previous surgery or radiation to treat the subject's Cushing syndrome. In certain embodiments, the subject has not had previous surgery or radiation to treat the subject's Cushing syndrome. In certain embodiments, the disease is Cushing's disease.

In certain embodiments, the disease is exogenous hypercortisolism. In certain embodiments, the disease is hypercortisolism. In certain embodiments, the disease is hyperglycemia. In certain embodiments, the disease is multiple endocrine neoplasia type 1. In certain embodiments, the disease is McCune Albright syndrome. In certain embodiments, the disease is Carney complex. In certain embodiments, the disease is congenital adrenal hyperplasia. In certain embodiments, the disease is precocious puberty.

In certain embodiments, the disease is a hormone-sensitive cancer. In certain embodiments, the disease is prostate cancer and other androgen-sensitive cancers. In certain embodiments, the disease is breast cancer, ovarian cancer or another cancer sensitive to estrogen or progesterone.

In certain embodiments, the disease is a disorder susceptible of treatment by levoketoconazole, or a pharmaceutically acceptable salt thereof.

In certain embodiments, the titration scheme comprises the up-titration of the levoketoconazole, or a pharmaceutically acceptable salt thereof until one or more of the following conditions are met: (1) the subject has an adequate response; (2) the highest label-specified dose is reached; or (3) a dose limiting event occurs.

In certain embodiments, the titration scheme comprises administering a first dose of the levoketoconazole, or a pharmaceutically acceptable salt thereof, for a first time period, such as about one week; increasing the dose by an amount equal to an incremental value; and determining whether the subject tolerates the increased dose; wherein the cycle is repeated so long as the subject tolerates the increased dose, wherein the incremental value at each cycle repetition is the same or different; and wherein if the subject does not tolerate the increased dose, the dose for the patient is equal to the difference between the further increased dose and the incremental value for the last cycle repetition. In certain embodiments, the initial dose of levoketoconazole, or a pharmaceutically acceptable salt thereof, is 150 mg twice daily. In certain embodiments, the incremental value is 150 mg.

In certain embodiments, the highest protocol-specified dose is 1200 mg/day. In certain embodiments, the subject may receive a dose of between 150 mg twice daily and to 600 mg twice daily. In certain embodiments, the dose is 150 mg once daily. In certain embodiments, the therapeutically effective amount of the levoketoconazole, or a pharmaceutically acceptable salt thereof, is between 150 mg and 1200 mg per day. In certain embodiments, the therapeutically effective amount of the levoketoconazole, or a pharmaceutically acceptable salt thereof, is 150 mg once daily. In certain embodiments, the therapeutically effective amount of the levoketoconazole, or a pharmaceutically acceptable salt thereof, is 150 mg twice daily. In certain embodiments, the therapeutically effective amount of the levoketoconazole, or a pharmaceutically acceptable salt thereof, is 300 mg twice daily. In certain embodiments, the therapeutically effective amount of the levoketoconazole, or a pharmaceutically acceptable salt thereof, is 450 mg twice daily. In certain embodiments, the therapeutically effective amount of the levoketoconazole, or a pharmaceutically acceptable salt thereof, is 600 mg twice daily.

In certain embodiments, the titration scheme comprises an initial reduction of dose. In certain embodiments, the initial dose of levoketoconazole, or a pharmaceutically acceptable salt thereof, is 150 mg twice daily and the reduced dose is 150 mg daily. In certain embodiments, after the initial reduction of dose, if the subject tolerates the reduced dose, the dose is then increased via a titration scheme as described herein. In certain embodiments, administration is maintained at 150 mg daily.

In certain embodiments, the titration scheme comprises the up-titration of the levoketoconazole, or a pharmaceutically acceptable salt thereof until the subject has an adequate response. In certain embodiments, an adequate response comprises normalization of urinary free cortisol (UFC) (e.g., 24-hour UFC, 4-hour UFC, 12-hour UFC, or other such UFC measurement) or late-night salivary cortisol (LNSC) or multiply-sampled serum cortisol (MSSC). In certain embodiments, UFC, LNSC or MSSC normalization comprises at least a 50% decrease in mean UFC. In certain embodiments, an adequate response is less than a 50% decrease from baseline cortisol levels. In certain embodiments, up-titration of the levoketoconazole is continued until at least two of the cortisol measurements chosen from UFC, LNSC and MSSC are below baseline cortisol levels, such as an at least 50% decrease from the baseline cortisol level. In certain embodiments, up-titration of the levoketoconazole is stopped when UFC, LNSC and MSSC are normalized or are below baseline cortisol levels. In certain embodiments, an adequate response comprises an improvement in hypercortisolism, such as that measured via hair cortisol or multiply-sampled sweat cortisol.

In certain embodiments, the titration scheme further comprises a maintenance phase wherein the subject is administered a therapeutically effective amount of levoketoconazole at a fixed dose.

In certain embodiments, the titration scheme comprises the up-titration of the levoketoconazole, or a pharmaceutically acceptable salt thereof, until the subject experiences a dose limiting event. In certain embodiments, after the subject experiences a dose limiting event, the method further comprises reducing the dose of levoketoconazole, or a pharmaceutically acceptable salt thereof. In certain embodiments, after the subject experiences a dose limiting event, the method further comprises temporarily interrupting administration of the levoketoconazole, or a pharmaceutically acceptable salt thereof, until the dose limiting event is reversed and then resuming administration of the levoketoconazole, or a pharmaceutically acceptable salt thereof, at the same or a reduced dose. In certain embodiments, administration of the levoketoconazole, or a pharmaceutically acceptable salt thereof, is not resumed.

In certain embodiments, the dose limiting event is due to the increased exposure to the MATE1 substrate or OCT2 substrate. In certain embodiments, the method further comprises informing the subject or a medical care worker that co-administration of the levoketoconazole, or a pharmaceutically acceptable salt thereof, and the MATE1 substrate or OCT2 substrate may result in increased exposure to MATE1 substrate or OCT2 substrate. In certain embodiments, the method further comprises informing the subject or a medical care worker that co-administration of the levoketoconazole, or a pharmaceutically acceptable salt thereof, and MATE1 substrate or OCT2 substrate may result in one or more exposure-related adverse reactions associated with administration of the MATE1 substrate or OCT2 substrate. In certain embodiments, the method further comprises monitoring the serum concentration of the MATE1 substrate or OCT2 substrate. In certain embodiments, the method further comprises monitoring the subject for one or more exposure-related adverse reactions associated with administration of the MATE1 substrate or OCT2 substrate.

In certain embodiments, the dose limiting event is due to the increased exposure to metformin. In certain embodiments, the method further comprises informing the subject or a medical care worker that co-administration of the levoketoconazole, or a pharmaceutically acceptable salt thereof, and metformin, or a pharmaceutically acceptable salt thereof, may result in increased exposure to metformin, or a pharmaceutically acceptable salt thereof. In certain embodiments, the method further comprises informing the subject or a medical care worker that co-administration of the levoketoconazole, or a pharmaceutically acceptable salt thereof, and metformin, or a pharmaceutically acceptable salt thereof, may result in one or more exposure-related adverse reactions associated with metformin administration. In certain embodiments, the method further comprises monitoring the serum concentration of metformin, or a pharmaceutically acceptable salt thereof. In certain embodiments, the method further comprises monitoring the subject for one or more exposure-related adverse reactions associated with metformin administration. These adverse reactions may be mild or moderate in severity. In certain embodiments, the method further comprises the one or more exposure-related adverse reactions are chosen from diarrhea, nausea/vomiting, flatulence, asthenia, indigestion, abdominal discomfort, lactic acidosis, and headache.

In certain embodiments, the dose limiting event is a QTc prolongation event. In certain embodiments, the QTc prolongation event comprises at least one QTc value representing greater than 60 msec increase from baseline. In certain embodiments, the QTc prolongation event comprises at least one confirmed QTc interval of greater than 470 msec, or in certain embodiments, at least one confirmed QTc interval of greater than 500 msec. In certain embodiments, the QTc prolongation event comprises an absolute QTc interval above 470 msec for males and above 480 msec for females. In certain embodiments, the QTc prolongation event comprises an absolute QTc interval above 60 msec above the baseline.

In certain embodiments, the method further comprises monitoring for an effect on the QTc interval.

In certain embodiments, the dose limiting event is an elevated liver function test (LFT). In certain embodiments, the LFT comprises tests analyzing one of more of the following analytes in serum: alanine transaminase (ALT), aspartate transaminase (AST), alkaline phosphatase (ALP), gamma glutamyl transferase (GGT), glutamate dehydrogenase (GLDH), lactate dehydrogenase (LDH) and/or bilirubin (unconjugated, conjugated or total). In certain embodiments, the elevated LFT is at least 1.5 times the upper limit of normal of the reference range. In certain embodiments, the elevated LFT is at least 2 times the upper limit of normal of the reference range. In certain embodiments, the elevation further comprises elevation of greater than one times the upper limit of normal of the reference range in either ALT or AST. To this effect, the normal range for a given analyte can vary based on testing methodology and from laboratory to laboratory. In certain embodiments, the method further comprises monitoring liver function.

In certain embodiments, the dose limiting event is an increased risk of Type B lactic acidosis. In certain embodiments, the dose limiting event is a blood pH less than 7.35 and lactate concentration of greater than 5 mmol/L. In some embodiments, the subject also has a reduced serum bicarbonate concentration (e.g., less than 22 mmol/L) and/or an anion gap of greater than 12 meQ/L.

In certain embodiments, the dose limiting event is abnormal kidney function. In certain embodiments, the method further comprises monitoring eGFR. In certain embodiments, abnormal kidney function comprises an estimated glomerular filtration rate (eGFR) of less than 30 mL/min/1.73 m$^2$. In certain embodiments, abnormal kidney function comprises an eGFR of 30-45 mL/min/1.73 m$^2$. In certain embodiments, if eGFR falls below 35 mL/min/1.73 m$^2$, the method further comprises discontinuing administration of metformin.

In certain embodiments, the dose limiting event is a decreased fasting glucose level. In certain embodiments, the dose limiting event is a risk of further hypoglycemia.

In certain embodiments, the dose limiting event is anion gap acidosis. In certain embodiments, the dose limiting event is macrocytic anemia secondary to low vitamin B-12.

In certain embodiments, the MATE1 substrate is chosen from the substrates (or pharmaceutically acceptable salts thereof) shown below:

| MATE1 Substrate | Associated Disease or Disorder |
|---|---|
| Acyclovir | A guanosine analog used to treat herpes simplex, varicella zoster, herpes zoster. |
| Cimetidine | A histamine H2 receptor antagonist used to manage GERD, peptic ulcer disease, and indigestion. |
| Ciprofloxacin | Oral, intravenous, intratympanic, ophthalmic, and otic administration for a number of bacterial infections |
| Estrone sulfate | Treatment of moderate to severe vasomotor symptoms associated with the monopause, and moderate to severe symptoms of vulval and vaginal atrophy associated with the menopause. |
| Flecainide | Prevent supraventricular arrhythmias, ventricular arrhythmias and paroxysmal atrial fibrillation and flutter |
| Ganciclovir | A DNA polymerase inhibitor used to treat cytomegalovirus and herpetic keratitis of the eye. |
| Guanidine | For the reduction of the symptoms of muscle weakness and easy fatigability associated with the myasthenic syndrome of Eaton-Lambert |
| Levofloxacin | Treatment of bacterial conjunctivitis caused by susceptible strains of the following organisms: Corynebacterium species, Staphylococcus aureus, Staphylococcus epidermidis, Streptococcus pneumoniae, Streptococcus (Groups C/F/G), Viridans group streptococci, Acinetobacter lwoffii, Haemophilus influenzae, Serratia marcescens |
| Metformin | A biguanide drug used in conjunction with diet and exercise for glycemic control in type 2 diabetes mellitus and used off-label for insulin resistance in polycystic ovary syndrome (PCOS). |
| Nadolol | Treat angina pectoris and hypertension |
| Procainamide | For the treatment of life-threatening ventricular arrhythmias. |
| Relebactam | In combination with imipenem and cilastatin for the treatment of complicated urinary tract infections, including pyelonephritis, and complicated intra-abdominal infections caused by susceptible organisms |
| Tipiracil | In combination with trifluridine, is indicated for the treatment of refractory mestastatic colorectal cancer patients who keep progressing despite of treatment with standard chemotherapy and biologics |
| Topotecan | An antineoplastic agent used to treat ovarian cancer, small cell lung cancer, or cervical cancer. |

In certain embodiments, the MATE1 substrate is chosen from cimetidine, abemacicilib, levofloxacin, ciprofloxacin, topotecan, metformin, cephalexin, acyclovir, cefradine, estrone sulfate, ganciclovir, guanidine, procainamide, and combinations thereof, or a pharmaceutically acceptable salt thereof. In certain embodiments, the MATE1 substrate is metformin, or a pharmaceutically acceptable salt thereof.

In certain embodiments, the OCT2 substrate is chosen from the substrates (or pharmaceutically acceptable salts thereof) shown below:

| OCT2 Substrate | Associated Disease or Disorder |
| --- | --- |
| Amantadine | For the chemoprophylaxis, prophylaxis, and treatment of signs and symptoms of infection caused by various strains of influenza A virus. Also for the treatment of parkinsonism and drug-induced extrapyramidal reactions |
| Choline | Nutritional supplementation, also for treating dietary shortage or imbalance |
| Choline salicylate | Relief of pain and discomfort of common mouth ulcers, cold sores, denture sore spots, infant teething and mouth ulcers, and sore spots due to orthodontic devices in children |
| Cimetidine | Treatment and the management of acid-reflux disorders (GERD), peptic ulcer disease, heartburn, and acid indigestion |
| Cisplatin | Treatment of metastatic testicular tumors, metastatic ovarian tumors and advanced bladder cancer |
| Dalfampridine | Neurofunctional modifier that helps improve walking speed in patients with multiple sclerosis |
| Dofetilide | Maintenance of normal sinus rhythm (delay in time to recurrence of atrial fibrillation/atrial flutter |
| Dopamine | Correction of hemodynamic imbalances present in the shock syndrome due to Myocardial infarction, trauma, endotoxic septicemia, open-heart surgery, renal failure, and chronic cardiac decompensation as in congestive failure |
| Epinephrine | Emergency treatment of allergic reactions (Type I) |
| Guanfacine | Treat ADHD |
| Histamine | Diagnostic aid for evaluation of gastric acid secretory function |
| Lamivudine | Treatment of HIV infection and chronic hepatitis B (HBV). |
| Linagliptin | Treatment of type II diabetes |
| Memantine | Manage moderate to severe Alzheimer's dementia |
| Metformin | Adjunct to diet and exercise to increase glycemic control in patients diagnosed with type 2 diabetes mellitus |
| Norepinephrine | Treat patients in vasodilatory shock states such as septic shock and neurogenic shock |
| Oxaliplatin | Treatment of advanced carcinoma of the colon or rectum and for adjuvant treatment of stage III colon cancer patients |
| Pramipexole | Symptomatic treatment of Parkinson's disease |
| Ranitidine | Treatment of short-term treatment of active duodenal ulcer, treating gastric acid hypersecretion due to Zollinger-Ellison syndrome, systemic mastocytosis, and other conditions that may pathologically raise gastric acid levels |
| Reserpine | Treatment of hypertension |
| Tipiracil | Treatment of refractory mestastatic colorectal cancer patients |
| Varenicline | Aid in smoking cessation |

In certain embodiments, the OCT2 substrate is chosen from amantadine, amiloride, cimetidine, dopamine, famotidine, memantine, metformin, pindolol, procainamide, ranitidine, varenicline, and oxaliplatin, or a pharmaceutically acceptable salt thereof. In certain embodiments, the OCT2 substrate is metformin, or a pharmaceutically acceptable salt thereof.

In certain embodiments, the dose of the MATE1 substrate or OCT2 substrate is decreased. In certain embodiments, the dose of the MATE1 substrate or OCT2 substrate is reduced by at least 5%, such as by at least 10%, by at least 20%, by at least 25%, by at least 30%, by at least 40%, by at least 50%, by at least 60%, by at least 70%, by at least 75%, by at least 80%, or by at least 90%. In certain embodiments, the frequency of administration of the MATE1 substrate or OCT2 substrate is decreased. For example, when the dose is not reduced, the frequency of administration might be extended from twice daily (BID) to once daily (QD), or to every other day (QOD), and on.

In certain embodiments, the dose of the metformin, or a pharmaceutically acceptable salt thereof, is decreased. In certain embodiments, the dose of the metformin, or a pharmaceutically acceptable salt thereof, is reduced by at least 5%, such as by at least 10%, by at least 20%, by at least 25%, by at least 30%, by at least 40%, by at least 50%, by at least 60%, by at least 70%, by at least 75%, by at least 80%, or by at least 90%. In certain embodiments, the frequency of administration of the metformin, or a pharmaceutically acceptable salt thereof, is decreased. For example, when the dose is not reduced, the frequency of administration might be extended from twice daily (BID) to once daily (QD), or to every other day (QOD), and on.

While the disclosed compounds may be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound disclosed herein or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In some embodiments, the dosage form is suitable for oral administration and contains one or more pharmaceutical excipients. In some embodiments, the unit dosage form is an immediate release tablet comprising 150 mg levoketoconazole together with microcrystalline cellulose, lactose, corn starch, colloidal silicon dioxide, and magnesium stearate. In some embodiments, the tablet is film coated.

Compounds may be administered orally or via injection at a dose of from 0.1 to 500 20 mg/kg per day. The dose range for adult humans is generally from 150 mg to 1.2 g/day. Tablets or other forms of presentation provided in discrete units may conveniently contain an amount of one or more compounds which is effective at such dosage or as a multiple of the same, for instance, units containing 150 mg to 1200 mg.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLE

Example 1—Drug-Drug Interaction Study with MATE1 and OCT2 Substrates

A study was designed to evaluate levoketoconazole as an inhibitor of MATE1 or OCT2. Compounds that are substrates or inhibitors of the transporters may be victims or perpetrators in drug-drug interactions. Experiments were carried out as described in the FDA and EMA draft guidance documents for Drug Interaction Studies (FDA 2017, EMA 2013). The probe substrate was [$^{14}$C]-metformin.

Short-term stability testing was performed on the test article solutions. Dose solutions at the low and high test article concentrations (e.g., 0.03 and 50 μM) were prepared in each incubation media and stored in the selected vessel type at room temperature and 37±2° C. for 6 hours. After the applicable storage duration, solutions at the same test article concentrations were re-prepared and analyzed with the previously stored samples to determine stability. Solutions were stable if the difference between mean responses (e.g., area ratios) for fresh and stored samples was within ±15% for dosing solutions.

The toxicity of the test articles to the various cell system in the study were assessed separately by measuring the lactate dehydrogenase (LDH) released from the cells. Incubation media not exposed to cells will serve as a background control. Incubation media were collected from cells exposed to no test article solvent control incubation media (containing only positive control substrate and inhibitor solvent, 0.2% v/v DMSO) (negative control), 1% Triton X-100 (positive control), solvent control (0 μM sample containing 0.2% v/v DMSO and test article solvent) and the test articles at select concentrations. Toxicity observed with the test articles was ≤25% compared to that of the positive control.

Stock solutions of the radiolabeled transporter substrates (e.g., 10 mM) were prepared in DMSO. [$^{14}$C]-Metformin (1 mM) was provided as a solid and was prepared in Hank's Balanced Salt Solution (HBSS). Control inhibitors were prepared in DMSO (e.g., 10 mM). The substrates and the control inhibitors or DMSO for the solvent control were spiked into incubation media in 0.1% v/v DMSO. The test article was spiked into the incubation media in an appropriate solvent and the solvent concentration was adjusted so the solvent was the same in all incubations.

The non-specific binding of the test articles to select incubation vessels absent cells was evaluated. The test articles were mixed with applicable incubation media, separately, at low and high concentrations and incubated in 24-well cell culture plates but absent cells. At the end the incubation period, aliquots of mixture were collected and analyzed by LC-MS/MS and compared to the dose solution (100% solution). A standard curve was be included. Recovery was determined from area ratio.

Before the experiment, cell culture plates (transporter-expressing and control cells) were removed from the incubator, the cell culture medium was removed and incubation medium (1 mL) was added to the plate to rinse the cell culture medium from the cells. Incubation medium was replaced with incubation medium containing levoketoconazole, positive control inhibitor or solvent control (0.3 mL) and the plates were preincubated. After preincubation, incubation medium was replaced with incubation medium containing levoketoconazole, positive control inhibitor or solvent control and the probe substrate. Samples were incubated for the designated time. After incubation, incubation medium was removed, and cells were rinsed once with 1 mL of ice-cold phosphate-buffered saline (PBS) containing 0.2% w/v bovine specific antigen (BSA) and twice with ice-cold PBS. The PBS was removed, and 0.5 mL of sodium hydroxide (0.1 M) was added and pipetted up and down to dissolve and suspend the cells. An aliquot of the medium was added to a 96-well plate, diluted with scintillation fluid and analyzed on a MicroBeta scintillation counter. The amount of protein in each incubation was determined by bicinchoninic acid analysis.

The uptake of the relevant probe substrate in transporter expressing cells and control cells in the presence and absence of a known inhibitor was the positive control. The transporter specific uptake of the probe substrate or the test article was determined by subtracting the uptake in the control cells from the uptake in the transporter expressing cells. $IC_{50}$ values were determined from the decrease in activity (e.g., percent of control) when inhibition exceeds 50% and calculated by non-linear regression with the four-parameter $IC_{50}$ equation. To calculate recovery, samples were taken from the incubation media at zero minutes (dose solution) and the final incubation time and calculated.

Human embryonic kidney 293 (HEK293) cells expressing transporter transfected with vectors containing human transporter cDNA for MATE1, OCT2, and control cells (HEK293 cells transfected with only vector) were used in experiments to evaluate levoketoconazole as an inhibitor of MATE1 or OCT2.

HEK293 cells were cultured in Dulbecco's modified Eagle's medium (DMEM) supplemented with fetal bovine serum (FBS, 8.9% v/v), antibiotic/antimycotic (0.89% v/v) and L-glutamine (1.79 mM) in a humidified culture chamber (37±1° C., 95±5% relative humidity, and 5±1% $CO_2$) in cell culture flasks. The medium was replaced every 2 to 3 days, and the cells were passaged when they became confluent. HEPES (Sigma-Aldrich, Saint Louis) was the incubation medium for OCT2-expressing HEK293 cells. Cell loss was not observed in incubations with OCT2-expressing HEK293 cells.

Caco-2 cells were cultured on a porous membrane in a transwell plate and allowed to form a confluent monolayer with tight junctions. The monolayer separates the apical and basolateral compartments of the transwell. Caco-2 cells were cultured in Eagle's minimal essential medium (EMEM) supplemented with FBS (8.9% v/v), non-essential amino acids (0.89% v/v) and penicillin-streptomycin (45 U/mL and 45 μg/mL, respectively) in a humidified culture chamber (37±1° C., 95±5% relative humidity, and 5±1% $CO_2$). The medium was replaced every 2 to 3 days, and the cells were passaged when they became confluent.

MDCKII cells were cultured on a porous membrane in a transwell plate and allowed to form a confluent monolayer with tight junctions. The monolayer separates the apical and basolateral compartments of the transwell. MDCKII cells were cultured in DMEM supplemented with FBS (10% v/v) and penicillin-streptomycin (45 U/mL and 45 μg/mL, respectively) in a humidified culture chamber (37±2° C., 95±5% relative humidity, and 5±1% $CO_2$) in cell culture flasks. The medium was replaced every 2 to 3 days, and the cells were passaged when they became confluent.

The tables below show the results of the inhibition experiments with ketoconazole and levoketoconazole. Where applicable, n is the number of replicates, NA is Not applicable, and SD refers to the standard deviation. Unless otherwise noted, values are triplicate determinations rounded to three significant figures with standard deviations rounded to the same degree of accuracy. Percentages are rounded to one decimal place except percentages ≥100, which are rounded to the nearest whole number.

TABLE 1

Ketoconazole OCT2 inhibition in HEK293 cells using [$^{14}$C]-metformin (10 μM) for the probe substrate

| Inhibitor | [Inhibitor] (μM) | Uptake (pmol/mg) Control | Uptake (pmol/mg) OCT2 | Background corrected uptake rate (pmol/mg/min) | % control | $IC_{50}$ parameters |
|---|---|---|---|---|---|---|
| Solvent control | 0 | 5.83 ± 0.56 | 243 ± 22 | 119 | 100 | $IC_{50}$: 1.52 μM Slope: 1.41 |
| Keto-conazole | 0.03 | 4.25 ± 0.13 | 190 ± 7 | 92.8 | 78.2 | Min: 0% |
|  | 0.1 | 3.76 ± 0.58 | 241 ± 34 | 119 | 100 | Max: 92.0% |
|  | 0.3 | 2.71 ± 0.90 | 219 ± 25 | 108 | 91.2 |  |
|  | 1 | 3.38 ± 2.37 | 127 ± 23 | 62.1 | 52.3 |  |
|  | 3 | 1.86 (n = 2) | 70.0 ± 8.9 | 34.1 | 28.7 |  |
|  | 10 | 2.33 ± 1.02 | 22.1 ± 3.1 | 9.87 | 8.3 |  |
|  | 30 | 1.54 ± 0.96 | 7.27 ± 1.82 | 2.86 | 2.4 |  |

TABLE 2

Levoketoconazole OCT2 inhibition in HEK293 cells using [$^{14}$C]-metformin (10 μM) for the probe substrate

| Inhibitor | [Inhibitor] (μM) | Uptake (pmol/mg) Control | Uptake (pmol/mg) OCT2 | Background corrected uptake rate (pmol/mg/min) | % control | $IC_{50}$ parameters |
|---|---|---|---|---|---|---|
| Solvent control | 0 | 4.14 ± 0.16 | 286 ± 23 | 141 | 100 | $IC_{50}$: 0.218 μM Slope: 0.970 |
| Levoketo-conazole | 0.03 | 5.10 ± 0.74 | 318 ± 46 | 156 | 111 | Min: 0% |
|  | 0.1 | 4.31 ± 0.33 | 247 ± 13 | 121 | 86.2 | Max: 127% |
|  | 0.3 | 3.35 ± 0.64 | 155 ± 11 | 75.9 | 53.9 |  |

TABLE 2-continued

Levoketoconazole OCT2 inhibition in HEK293 cells using [$^{14}$C]-metformin (10 μM) for the probe substrate

| Inhibitor | [Inhibitor] (μM) | Uptake (pmol/mg) Control | Uptake (pmol/mg) OCT2 | Background corrected uptake rate (pmol/mg/min) | % control | $IC_{50}$ parameters |
|---|---|---|---|---|---|---|
| | 1 | 2.26 ± 0.52 | 69.6 ± 7.7 | 33.7 | 23.9 | |
| | 3 | 1.95 ± 0.93 | 28.2 ± 6.0 | 13.1 | 9.3 | |
| | 10 | 1.88 ± 0.66 | 7.71 ± 1.34 | 2.91 | 2.1 | |
| | 30 | 1.61 ± 0.45 | 3.44 ± 2.05 | 0.915 | 0.6 | |

TABLE 3

Ketoconazole MATE1 inhibition in HEK293 cells using [$^{14}$C]-metformin (10 μM) for the probe substrate

| Inhibitor | [Inhibitor] (μM) | Uptake (pmol/mg protein) (Average ± SD) Control | Uptake (pmol/mg protein) (Average ± SD) MATE1 | Background corrected uptake rate (pmol/mg/min) | % Control | $IC_{50}$ parameters |
|---|---|---|---|---|---|---|
| No Solvent Control | 0 | 6.17 ± 1.43 | 508 ± 38 | 100 | NA | NA |
| Solvent Control | 0 | 5.27 ± 1.26 | 540 ± 33 | 107 | 100 | $IC_{50}$: 0.279 μM |
| Keto-conazole | 0.03 | 6.53 ± 1.52 | 453 ± 29 | 89.3 | 83.6 | Slope: 1.06<br>Min: 0% |
| | 0.1 | 3.90 ± 2.13 | 382 ± 27 | 75.6 | 70.8 | Max: 92.0% |
| | 0.3 | 4.58 ± 1.36 | 235 ± 8 | 46.1 | 43.1 | |
| | 1 | 3.06 ± 1.56 | 104 ± 2 | 20.2 | 18.9 | |
| | 3 | 1.90 ± 0.81 | 44.2 ± 2.2 | 8.46 | 7.9 | |
| | 10 | 2.48 ± 0.09 | 16.4 ± 0.6 | 2.79 | 2.6 | |
| | 25 | 1.90 ± 0.51 | 12.7 ± 1.5 | 2.17 | 2.0 | |

TABLE 4

Levoketoconazole MATE1 inhibition in HEK293 cells using [$^{14}$C]-metformin (10 μM) for the probe substrate

| Inhibitor | [Inhibitor] (μM) | Uptake (pmol/mg protein) (Average ± SD) Control | Uptake (pmol/mg protein) (Average ± SD) MATE1 | Background corrected uptake rate (pmol/mg/min) | % Control | $IC_{50}$ parameters |
|---|---|---|---|---|---|---|
| No Solvent Control | 0 | 5.66 ± 1.56 | 433 ± 18 | 85.5 | NA | NA |
| Solvent Control | 0 | 5.38 ± 0.55 | 437 ± 25 | 86.4 | 100 | $IC_{50}$: 0.248 μM |
| Levoketo-conazole | 0.03 | 5.25 ± 0.96 | 400 ± 18 | 79.0 | 91.4 | Slope: 0.941<br>Min: 0% |
| | 0.1 | 4.21 ± 0.74 | 316 ± 30 | 62.3 | 72.1 | Max: 104% |
| | 0.3 | 3.58 ± 1.56 | 210 ± 11 | 41.4 | 47.9 | |
| | 1 | 3.81 ± 0.16 | 101 ± 9 | 19.4 | 22.5 | |
| | 3 | 2.64 (n = 2) | 44.0 ± 5.6 | 8.28 | 9.6 | |
| | 10 | 1.82 (n = 2) | 13.6 ± 0.9 | 2.36 | 2.7 | |
| | 25 | 2.82 ± 1.22 | 7.72 ± 1.09 | 0.981 | 1.1 | |

As can be seen from the foregoing tables, levoketoconazole inhibited OCT2 with an $IC_{50}$ of 0.218 μM, which was more potent than racemic ketoconazole ($IC_{50}$=1.52 μM).

Example 2—Phase I Study of Levoketoconazole And Metformin Coadministration

This was a Phase I, open-label, 3-period, fixed-sequence study in 32 healthy male and female subjects (about 16 per sex) designed to evaluate the effect of levoketoconazole on the pharmacokinetics of a single 500 mg dose of metformin. The study consisted of a screening period of up to 21 days, a metformin-only treatment period (Period 1, Treatment A), a levoketoconazole dose escalation treatment period (Period 2) to achieve the dose level to be used in Period 3, and a metformin and levoketoconazole co-administration treatment period (Period 3, Treatment B). Urine was also collected prior to dose administration and in specified intervals (0-6 hours, 6-12 hours, 12-24 hours, 24-36 hours, and 36-48 hours post-dose) for 48 hours after dose administration to measure the recovery of metformin.

All subjects received a single oral dose of 500 mg metformin in Period 1.

Period 2 was a dose escalation period designed to increase the levoketoconazole dose stepwise to the levoketoconazole dose level of 600 mg taken every 12 hours (Q12H) used in Period 3. Period 2 lasted from Day 4 to 27 of the study. Subjects received 150 mg, 300 mg, 450 mg, and 600 mg levoketoconazole Q12H (approximate timing when at home) as four consecutive weekly escalation cycles, starting on Day 4 with dose level 1. For dose level 1, subjects received 150 mg Q12H. For dose levels 2 and 3, subjects received 300 mg and 450 mg levoketoconazole Q12H, respectively. For dose level 4, subjects received 600 mg levoketoconazole Q12H. Subjects received 6 doses of 600 mg levoketoconazole alone before co-administration of levoketoconazole and metformin in Period 3.

Period 3 was the drug-drug interactions assessment period in which levoketoconazole 600 mg was co-administered with a single oral dose of 500 mg metformin on the morning of Day 28. Subjects received five repeated oral doses of 600 mg levoketoconazole Q12H for a total daily dose of 1200 mg. Period 3 lasted from day 28 to 31 of the study. Again, urine was collected prior to dose administration and in specified intervals (0-6 hours, 6-12 hours, 12-24 hours, 24-36 hours, and 36-48 hours post-dose) for 48 hours after dose administration to measure the recovery of metformin.

The preliminary metformin pharmacokinetic parameters are described in Table 5. There is an increase in Cmax and AUC, as well as a decrease in Cl/F in Period 3.

TABLE 5

| Period | | Cmax (ng/mL) | Tmax (h) | AUClast (h*ng/mL) | Tlast (h) | AUCINF (h*ng/mL) | Vz/F (L) | Cl/F (L/h) | t1/2 (h) |
|---|---|---|---|---|---|---|---|---|---|
| 1 | N | 30 | 30 | 30 | 30 | 19 | 19 | 19 | 19 |
| | Median | 822 | 4.00 | 6450 | 48.0 | 6270 | 1350 | 79.7 | 12.1 |
| | Geometric Mean | 844 | NC | 6280 | NC | 6090 | 1340 | 82.2 | 11.3 |
| | CV % Geometric Mean | 20.8 | NC | 17.7 | NC | 14.2 | 66.7 | 14.2 | 55.00 |
| 3 | N | 17 | 17 | 17 | 17 | 16 | 16 | 16 | 16 |
| | Median | 1570 | 4.00 | 14600 | 48.0 | 15100 | 521 | 33.1 | 10.7 |
| | Geometric Mean | 1520 | NC | 13800 | NC | 14000 | 547 | 35.7 | 10.6 |
| | CV % Geometric Mean | 19.4 | NC | 24.2 | NC | 25.1 | 37.7 | 25.1 | 23.5 |

A comparison of Metformin co-administered with levoketoconazole in Period 3 vs. metformin alone in Period 1 was undertaken. A summary of the levoketoconazole effect on the pharmacokinetics of metformin is shown in Table 6. Administration of levoketoconazole increases the systemic exposure to metformin by about 2-fold.

TABLE 6

| Parameter | Units | N | n | Geometric LSM (Test) | Geometric LSM (Reference) | Test/Reference (%) | 90% Confidence Interval |
|---|---|---|---|---|---|---|---|
| AUCinf | h*ng/mL | 17 | 30 | 13900 | 6330 | 2.2 | (2.03, 2.39) |
| AUClast | h*ng/mL | 17 | 30 | 13800 | 6270 | 2.19 | (2.02, 2.37) |
| CLr | L/h | 17 | 30 | 9.61 | 25.6 | 0.375 | (0.308, 0.456) |
| Cmax | ng/mL | 17 | 30 | 1530 | 844 | 1.81 | (1.67, 1.96) |

A comparison of urine pharmacokinetic parameters from Metformin co-administered with levoketoconazole in Period 3 vs. metformin alone in Period 1 was undertaken, with the results shown in Table 7.

TABLE 7

| Treatment Period | Ae (ug) | Fe (%) | CLr (L/h) |
|---|---|---|---|
| Period 1 (n = 30) | 161000 (34.7) [142000, 182000] | 32.2 (34.7) [28.4, 36.5] | 25.6 (31.5) [22.9, 28.8] |
| Period 3 (n = 17) | 132000 (57.7) [99900, 173000] | 26.3 (57.7) [20.0, 34.7] | 9.54 (65.5) [7.02, 13.0] |

The plasma data and the additional pharmacokinetics parameters from plasma support a drug interaction between levoketoconazole and metformin via a mechanism of decreased total body clearance of metformin. The additional urine data support an effect of levoketoconazole to reduce urine clearance of metformin. Metformin is not metabolized and is excreted unchanged primarily if not exclusively in urine.

These previously undescribed effects of levoketoconazole to inhibit OCT2 in vitro, coupled with novel effect of co-administration of the drugs on metformin renal and total body clearances and urine excretion, and the magnitude of the increase in metformin AUC/Cmax that results from inhibition of clearance are unpredictable and clinically significant.

The various embodiments described above can be combined to provide further embodiments. All the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. A method of treating persistent or recurrent Cushing's syndrome in a subject in need thereof, wherein the subject is being coadministered an organic cation transporter 2 (OCT2) substrate, or a pharmaceutically acceptable salt thereof, comprising:
   administering a therapeutically effective amount of levoketoconazole, or a pharmaceutically acceptable salt thereof, to the subject in need thereof, wherein the therapeutically effective amount of levoketoconazole, or a pharmaceutically acceptable salt thereof, is determined via a titration scheme;
   during the levoketoconazole titration scheme, monitoring the subject for a dose limiting event, wherein the dose limiting event is due to increased exposure to the OCT2 substrate; and
   if the subject experiences a dose limiting event, reducing the amount of the OCT2 substrate, or a pharmaceutically acceptable salt thereof, administered to the subject.

2. The method of claim 1, wherein the dose limiting event is an elevated liver function test (LFT), a QTc prolongation event, abnormal kidney function, increased risk of Type B lactic acidosis, decreased fasting glucose level, anion gap acidosis, or low vitamin B-12.

3. The method of claim 1, wherein the subject has had previous surgery or radiation to treat the subject's persistent or recurrent Cushing's syndrome.

4. The method of claim 1, wherein the subject has not had previous surgery or radiation to treat the subject's persistent or recurrent Cushing's syndrome.

5. The method of claim 1, wherein reducing the amount of the OCT2 substrate, or a pharmaceutically acceptable salt thereof, comprises reducing the dose of the OCT2 substrate, or a pharmaceutically acceptable salt thereof, and maintaining the frequency of administration of the OCT2 substrate, or a pharmaceutically acceptable salt thereof.

6. The method of claim 5, wherein the dose of the OCT2 substrate, or a pharmaceutically acceptable salt thereof, is reduced by at least 25%.

7. The method of claim 5, wherein the dose of the OCT2 substrate, or a pharmaceutically acceptable salt thereof, is reduced by at least 50%.

8. The method of claim 1, wherein reducing the amount of the OCT2 substrate, or a pharmaceutically acceptable salt thereof, comprises maintaining the dose of the OCT2 substrate, or a pharmaceutically acceptable salt thereof, and reducing the frequency of administration of the OCT2 substrate, or a pharmaceutically acceptable salt thereof.

9. The method of claim 1, wherein the titration scheme comprises:
   administering a first dose of the levoketoconazole, or a pharmaceutically acceptable salt thereof, for a first time period;
   increasing the dose by an amount equal to an incremental value of 150 mg daily; and
   determining whether the subject tolerates the increased dose;
   wherein the cycle is repeated so long as the subject tolerates the increased dose; wherein the incremental value at each cycle repetition is the same or different; and wherein if the subject does not tolerate the increased dose, the dose for the patient is equal to the difference between the further increased dose and the incremental value for the last cycle repetition.

10. The method of claim 9, wherein the first dose of the levoketoconazole, or a pharmaceutically acceptable salt thereof, is 150 mg administered twice daily.

11. The method of claim 1, wherein the therapeutically effective amount of the levoketoconazole, or a pharmaceutically acceptable salt thereof, is between 150 mg and 1200 mg per day.

12. The method of claim 1, wherein the therapeutically effective amount of the levoketoconazole, or a pharmaceutically acceptable salt thereof, is 600 mg twice daily.

13. The method of claim 1, further comprising informing the subject or a medical care worker that co-administration of the levoketoconazole, or a pharmaceutically acceptable salt thereof, and the OCT2 substrate, or a pharmaceutically acceptable salt thereof, may result in increased exposure to the OCT2 substrate.

14. The method of claim 1, further comprising informing the subject or a medical care worker that co-administration of the levoketoconazole, or a pharmaceutically acceptable salt thereof, and the OCT2 substrate, or a pharmaceutically acceptable salt thereof, may result in one or more exposure-related adverse reactions associated with administration of the OCT2 substrate, or a pharmaceutically acceptable salt thereof.

15. The method of claim 1, further comprising monitoring the subject for one or more exposure-related adverse reactions associated with the OCT2 substrate, or a pharmaceutically acceptable salt thereof.

16. The method of claim 15, wherein the one or more exposure-related adverse reactions are chosen from diarrhea, nausea/vomiting, flatulence, asthenia, indigestion, abdominal discomfort, lactic acidosis, and headache.

17. The method of claim 1, wherein the OCT2 substrate is amantadine, choline, choline salicylate, cimetidine, cisplatin, dalfampridine, dofetilide, dopamine, epinephrine, guanfacine, histamine, lamivudine, linagliptin, memantine, norepinephrine, oxaliplatin, pramipexole, ranitidine, reserpine, tipiracil, or varenicline, or a pharmaceutically acceptable salt thereof.

18. The method of claim 1, wherein the OCT2 substrate is amantadine, amiloride, cimetidine, dopamine, famotidine, memantine, pindolol, procainamide, ranitidine, varenicline, or oxaliplatin, or a pharmaceutically acceptable salt thereof.

* * * * *